May 7, 1963 M. KRILOFF Plant Pat. 2,258
ROSE PLANT
Filed March 20, 1962
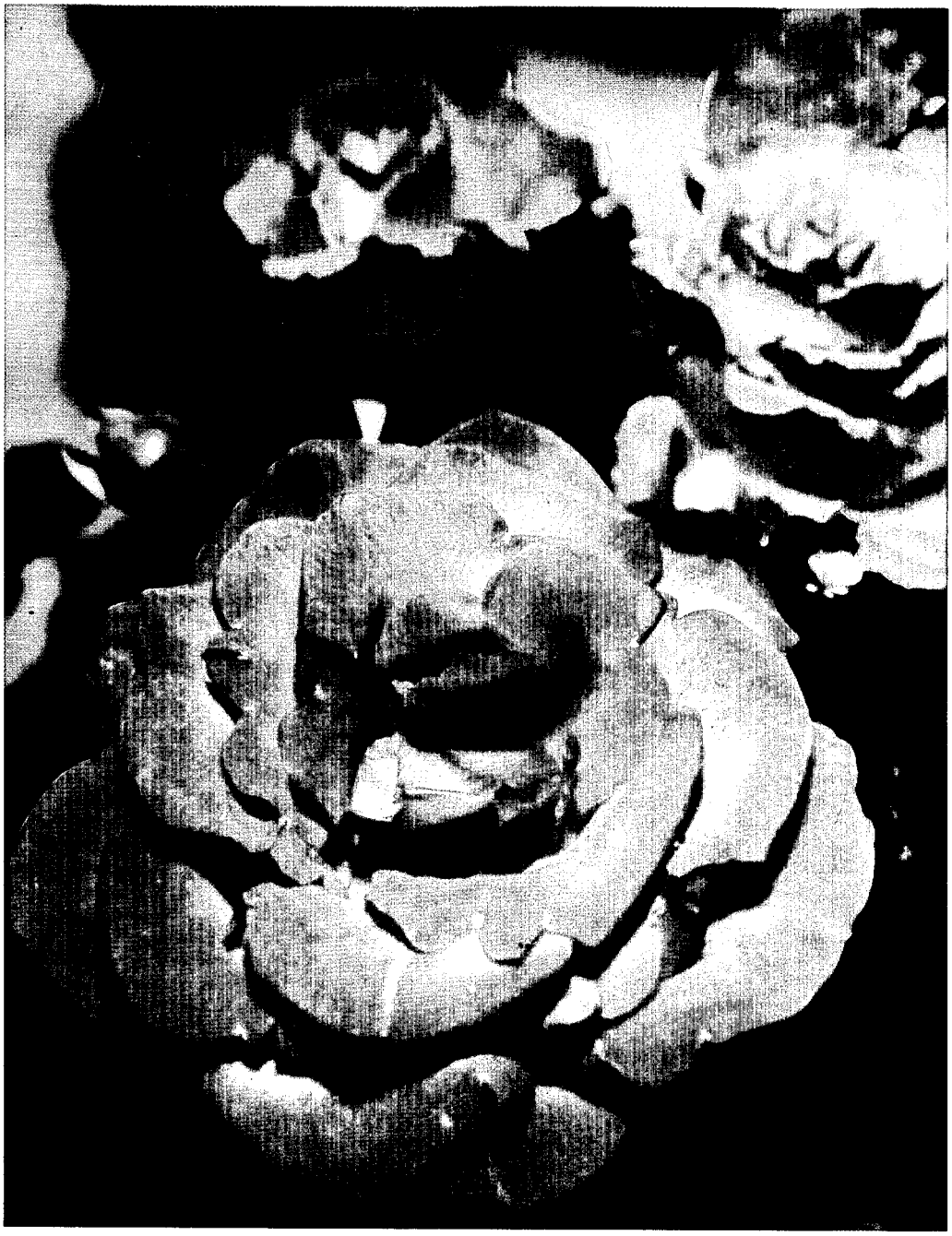
Inventor.
Michel Kriloff
By: Robb & Cobb
Attorneys.

United States Patent Office

Plant Pat. 2,258
Patented May 7, 1963

2,258
ROSE PLANT

Michel Kriloff, Antibes, Alpes-Maritimes, France, assignor to Ilgenfritz Nurseries, Inc., Monroe, Mich., a corporation of Michigan Filed Mar. 20, 1962, Ser. No. 181,218
1 Claim. (Cl. 47—61)

The present invention relates to a new and distinct variety of rose plant of the hybrid tea class, which was originated by me by crossing the variety known in the United States as "Peace," but known in France and Belgium as "Mme. A. Meilland" (U.S. Plant Patent No. 591) with the variety known as "Baccara" (U.S. Plant Plant No. 1,367).

As the result of this breeding, I have produced a new variety of rose plant which is distinguished from its parents, as well as from all other varieties of which I am aware, as evidenced by the following unique combination of characteristics which are outstanding in the new variety:

(1) A strong and vigorous habit of growth;
(2) Very good resistance to mildew and blackspot;
(3) Abundant production of blooms;
(4) Large and well shaped blooms;
(5) A symmetrical arrangement of the flower petals resembling a rose window; and
(6) A very vivid and very luminous red general color tonality of the flowers.

Asexual reproduction of my new variety by grafting, as performed at Antibes, France, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with Rene Oberthur's Repertoire de Couleurs, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—"Peace" (also known as "Mme. A. Meilland" in France and Belgium).
*Pollen parent.*—"Baccara."
Propagation: Holds its distinguishing characteristics through succeeding propagations by grafting.

*Flower*

Locality where grown and observed: Antibes, France.
Continuity: Continuous.
Fragrance: Slight. Nature—tea.
Flowers borne: Both singly and in regular cluster; on strong stems of medium length.
Quantity of bloom: Free and abundant, outdoors.
Bud:
*Peduncle.*—Medium caliper; erect; stiff; with few brown hairs. Color—green-bronze.
*Before calyx breaks.*—Size—Medium. Form—from pointed to globular; with a conspicuous neck; with foliaceous appendages on the surface of the bud; with slender, much-cut, bristle-like foliaceous parts extending beyond the tip of the bud equal to ½ of its length. Color—Rouge Sang-de-Boeuf, Plate 94–4.
*As calyx breaks.*—Color—Rouge Andrinople, Plate 92–1.
*As first petal opens.*—Size—from medium to large. Form—short; ovoid. Color: outside—Rouge Andrinopole, Plate 92–1; inside—Rouge Neyron, Plate 119–3.
*Opening.*—Opens up well; is retarded from opening by cold weather.
Bloom:
*Size (when fully open).*—Large; from 5 to 7 inches.
*Petalage.*—Very double; from 35 to 45 petals; arranged regularly in roseate form.
*Form.*—Cupped and globular at first but becoming open-cupped; petals being at first very loosely rolled inward, but later becoming cupped and rolled outward at maturity.
Petals:
*Texture.*—Thick.
*Appearance.*—Inside—shiny - satiny. Outside—shiny-satiny.
*Shape.*—Outside—round; scalloped; with apex flat. Intermediate—round; scalloped; with apex flat. Inside—oval; scalloped; with apex flat.

This description of a newly opened flower was made from a rose grown outdoors during the month of June at Antibes, France:

*Color*—Outer petal: outside surface—Rouge Sang-de-Boeuf, Plate 94–3; inside surface—Rouge Sang-de-Boeuf, Plate 94–4. Intermediate petal: outside surface—Rouge Andrinople, Plate 92–1; inside surface—Rouge Andrinople; Plate 92–1. Inner petal: outside surface—Rouge Neyron, Plate 119–3; inside surface—Rouge Neyron, Plate 119–3.

This description was made from a rose that was open for three days outdoors during the month of June at Antibes, France:

*Color.*—Outer petal: outside surface—Rouge Sang-de-Boeuf, Plate 94–3; inside surface—Rouge Sang-de-Boeuf, Plate 94–4. Inner petal: outside surface—Rouge Andrinople, Plate 92–1; inside surface—Rouge Andrinople, Plate 92–1.
*General color effect.*—Newly opened flower—Rouge Andrinople, Plate 92–2. Three days open—Rouge Geranium, Plate 111–1.
*Behavior.*—Persistent; cold weather delays opening of flowers.
*Flower longevity.*—On bush in garden—5 days during April, May and June. Cut roses grown outdoors and kept at living room temperatures—5 or 6 days during April, May and June.

*Reproductive Organs*

Stamens: Very many; irregularly arranged about pistils. Color—Jaune primevere, Plate 19–2.
Filaments: Medium length, with anthers.
Anthers: Large; all open at once. Color—yellow.
Pollen: Moderate abundance. Color—lemon-gold.
Pistils: From medium number to many; long.
Styles: Uneven; long; thin; bunched.
Stigma: Color—yellow.
Ovaries: All enclosed in calyx.
Hips: Pointed; smooth; fleshy. Color—green and reddish.
Sepals: Permanent; long; spear-shaped. Color—Vert, Plate 298–4.
Seeds: Many; large.

*Plant*

Foliage:

*Leaves.*—Compound of usually 5, but sometimes 7 leaflets; normal abundance; medium large size; glossy.

*Leaflets.*—Shape—ovoid, with apex obtuse. Base—round. Margin—very dentate.

*Color.*—Mature: upper surface—dark green; under surface—green-bronze, with nerves very marked. Young: upper surface—red; under surface—light red.

*Rachis (the supporting stem of the compound leaf).*—Medium caliper. Upper side—grooved. Under side—sparsely prickly; round.

*Stipules.*—Medium length; moderately narrow; with points of medium length turning out at an angle of less than 45° and recurved toward the stem.

*Disease resistance.*—Very good resistance to mildew and blackspot as determined by comparison with other varieties grown under comparable cultural conditions at Antibes, France.

Growth:

*Habit.*—Bushy; upright; much-branched.

*Growth.*—Free; vigorous.

*Canes.*—Medium caliper.

*Main stems.*—Color—from brown to bronze-red. Thorns—several; medium length; hooked downward; with long, narrow base. Prickles—few. Hairs—none.

*Branches.*—Color—from green-brown to bronze-red. Thorns—few; hooked downward; with narrow base. Prickles—few; color—brown. Hairs—none.

*New shoots.*—Color—bright bronze-red. Thorns—few; medium length; hooked downward; with broad base. Prickles—several; color—reddish. Hairs—none.

I claim:

A new and distinct variety of rose plant of the hybrid tea class, substantially as herein shown and described, characterized particularly as to novelty by the unique combination of a strong and vigorous habit of plant growth; very good resistance to mildew and blackspot, abundant bloom production, large and well-shaped flower form; a symmetrical flower petal arrangement resembling a rose window, and a very vivid and very luminous red general color tonality of the flowers.

No references cited.